(12) United States Patent
Gürtler et al.

(10) Patent No.: US 6,420,616 B1
(45) Date of Patent: Jul. 16, 2002

(54) PROCESS FOR PREPARING A DINITRONAPHTHALENE ISOMER MIXTURE HAVING AN INCREASED PROPORTION OF 1,5- DINITRONAPHTHALENE

(75) Inventors: Christoph Gürtler, Köln; Manfred Jautelat, Burscheid; Michael Schelhaas, Köln, all of (DE)

(73) Assignee: Bayer Aktiengesellschaft, Leverkusen (DE)

( * ) Notice: Subject to any disclaimer, the term of this patent is extended or adjusted under 35 U.S.C. 154(b) by 0 days.

(21) Appl. No.: 09/726,241

(22) Filed: Nov. 29, 2000

(30) Foreign Application Priority Data

Dec. 3, 1999 (DE) .......................... 199 58 389

(51) Int. Cl.⁷ ............................................ C07C 205/00
(52) U.S. Cl. .................. 568/931; 568/928; 568/930
(58) Field of Search ................................ 568/931, 928, 568/930

(56) References Cited

U.S. PATENT DOCUMENTS 6,242,656 B1 * 6/2001 Steinlein et al. ............. 568/930

FOREIGN PATENT DOCUMENTS

| DE | 1 150 965 | 7/1963 |
| DE | 1150965 | 7/1963 |
| DE | 24 53 529 | 5/1976 |
| WO | 94/19310 | 9/1994 |
| WO | 99/12887 | 3/1999 |
| WO | 00/32572 | 6/2000 |
| WO | 01/09065 | 2/2001 |

OTHER PUBLICATIONS

G.A. Olah et al, Nitration: Methods and Mechanisms, VCH, New York, (month unavailable) 1989, Chapter 1. Introduction and General Aspects, pp. 1–8.

* cited by examiner

*Primary Examiner*—Jafar Parsa
(74) *Attorney, Agent, or Firm*—Joseph C. Gil; Richard E. L. Henderson

(57) ABSTRACT

The present invention relates to a process for preparing a dinitronaphthalene isomer mixture having an increased proportion of 1,5-dinitronaphthalene by nitrating naphthalene in the presence of at least one ionic liquid.

9 Claims, No Drawings

PROCESS FOR PREPARING A DINITRONAPHTHALENE ISOMER MIXTURE HAVING AN INCREASED PROPORTION OF 1,5- DINITRONAPHTHALENE

BACKGROUND OF THE INVENTION

The invention relates to the preparation of a dinitronaphthalene isomer mixture having an increased proportion of 1,5-dinitronaphthalene by direct nitration of naphthalene. 1,5-Dinitronaphthalene is a key compound for the preparation of 1,5-diaminonaphthalene. This is, inter alia, the starting compound for the preparation of 1,5-diisocyanato-naphthalene (trade name Desmodur 15®). 1,5-Diisocyanato-naphthalene is used as an isocyanate component in polyurethane production.

The preparation of nitrated aromatics has been known for a long time (G. A. Olah et al., *Nitration: Methods and Mechanism*, VCH, New York, 1989). For decades, nitroaromatics have been prepared industrially by nitration using a mixture of sulfuric and nitric acids (known as mixed or nitration acid).

The nitration of naphthalene in mixed acid at elevated temperatures of from 80 to 100° C. gives a mixture of various dinitronaphthalenes. This mixture comprises mainly 1,5- and 1,8-dinitronaphthalene in a ratio of about 1:2. In addition, the mixture contains about 5% of other isomers, for example 1,6- and 1,7-dinitronaphthalene. The unfavorable selectivity of the reaction thus leads to a high and undesirable proportion of 1,8-dinitronaphthalene being preferentially formed in the preparation of 1,5-dinitronaphthalene.

German Offenlegungsschrift 11 50 965 describes the preparation of 1,5-dinitronaphthalene starting from 1-nitronaphthalene. An increase in the selectivity in favor of the desired of 1,5 isomer is achieved by rapid and intensive mixing of the 1-nitronaphthalene dissolved in sulfuric acid with nitration acid. Disadvantages of this process are the considerable amount of sulfuric acid and its complicated and costly work-up. In addition, this process can form considerable amounts of trinitrated products that not only significantly reduce the yield of 1,5-dinitronaphthalene but also are critical in terms of safety, particularly under the adiabatic reaction conditions described in this prior art.

WO 99/12887 describes a process for preparing a dinitronaphthalene isomer mixture having an increased proportion of 1,5-dinitronaphthalene, likewise starting from 1-nitronaphthalene. Here, the reaction of the nitronaphthalene with nitric acid takes place in the presence of a solid perfluorinated strong acid ion exchanger. This process generally has the disadvantage that the resulting dinitronaphthalene isomer mixture must be separated from the catalyst by extraction with dioxane at 900° C. The dioxane subsequently must be removed by means of an additional distillation step. The best selectivities in respect of the desired 1,5 isomer are obtained when sulfolane or nitromethane is added as solvent. However, the conversion in the reaction is then only 31–44% and the reaction forms considerable amounts of other dinitro isomers and trinitrated naphthalenes, which are more difficult to separate from the isomer mixture.

German Offenlegungsschrift 24 53 529 describes the preparation of dinitronaphthalenes from naphthalene by nitration using nitric acid in organic solvents (for example, dichloroethane) and removal of the water of reaction by azeotropic distillation. This process gives dinitronaphthalene in high yields, but the isomer ratio is not influenced.

WO 94/19310 describes nitrations of nitroaromatics over aluminum silicates that are sometimes doped with heavy metals, known as claycops, as solid catalyst, giving high yields of dinitrated products with small amounts of trinitroaromatics. However, nitrations of naphthalene carried out by this process give isomer ratios similar to those in classic nitrations using mixed acid.

It is therefore an object of the invention to provide a process for preparing a dinitronaphthalene isomer mixture by nitration of naphthalene that gives a high conversion and a low proportion of by-products and at the same time forms a mixture of 1,5- and 1,8-dinitronaphthalene that contains an increased proportion of 1,5 isomer.

It has now surprisingly been found that the presence of ionic liquids in the nitration of naphthalene in an excess of nitric acid or a mixture of nitric acid and sulfuric acid and/or phosphoric acid makes it possible to shift the isomer ratio in favor of 1,5-dinitronaphthalene.

SUMMARY OF THE INVENTION

The invention accordingly provides a process for preparing a dinitronaphthalene isomer mixture having an increased proportion of 1,5-dinitronaphthalene comprising nitrating naphthalene with a molar excess of nitric acid in the presence of at least one ionic liquid.

DETAILED DESCRIPTION OF THE INVENTION

The dinitronaphthalene isomer mixtures prepared according to the invention contain, in addition to 1,8-dinitronaphthalene, a surprisingly high proportion of 1,5-dinitronaphthalene. The 1,5-dinitronaphthalene content is preferably above 30% by weight, based on the conversion, particularly preferably in the range from 35 to 40% by weight. The content of by-products, in particular 1,6- and 1,7-dinitronaphthalene and more highly nitrated products, is low.

In the process of the invention nitric acid is preferably used in a 1-to 22-fold molar excess, particularly preferably in a 2- to 20-fold molar excess, very particularly preferably in a 4- to 16-fold molar excess, based on the nitro groups to be introduced into naphthalene.

The concentration of the nitric acid used in the process of the invention is preferably from 50 to 100%, particularly preferably from 60 to 100%, very particularly preferably from 67 to 98%.

In a further embodiment of the process of the invention, the nitric acid can be used in admixture with sulfuric acid and/or phosphoric acid.

If sulfuric acid is used in the process of the invention, its concentration is preferably from 90 to 100%, particularly preferably from 96 to 100% and very particularly preferably from 98 to 100%. If phosphoric is used in the process of the invention, its concentration is preferably from 50 to 99%, particularly preferably from 65 to 99% and very particularly preferably from 85 to 99%.

If a mixture of nitric acid and sulfuric acid and/or phosphoric acid is used in the process of the invention, this mixture preferably contains from 1 to 20 molar parts of nitric acid and 1 molar part of sulfuric acid and/or phosphoric acid, particularly preferably from 1 to 10 molar parts of nitric acid and 1 molar part of sulfuric acid and/or phosphoric acid, very particularly preferably from 1 to 5 molar parts of nitric acid and 1 molar part of sulfuric acid and/or phosphoric acid.

The ionic liquids used in the process of the invention are liquid salts of the formula $Q^+ A^-$ that preferably form liquid salts at temperatures below 90° C., in particular at temperatures below 80° C. and particularly preferably at temperatures below 50° C.

In the formula Q⁺ A⁻, Q⁺ preferably represents a quaternary ammonium and/or phosphonium ion. Q⁺ is particularly preferably a compound selected from the group consisting of

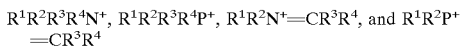

wherein $R^1$ to $R^4$ are, independently of one another, hydrogen (with the proviso that $R^1R^2R^3R^4N^+$ cannot be $NH_4^+$), saturated or unsaturated $C_1$–$C_{12}$-alkyl, $C_3$–$C_8$-cycloalkyl, $C_6$–$C_{10}$-aryl, or $C_7$–$C_{11}$-aralkyl.

Q⁺ is particularly preferably an ammonium and/or phosphonium ion derived from a nitrogen- and/or phosphorus-containing heterocycle containing 1, 2, or 3 nitrogen and/or phosphorus atoms and corresponding to the following formulas

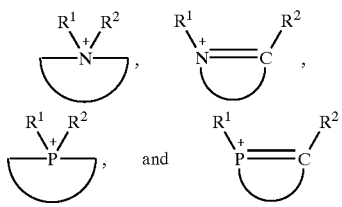

wherein the ring contains from 4 to 10 atoms (preferably 5 or 6 atoms) and $R^1$ and $R^2$ are as defined above.

Furthermore, Q⁺ preferably represents quaternary ammonium and/or phosphonium ions selected from the group consisting of

wherein $R^1$, $R^2$, and $R^3$ are identical or different and are as defined above, and $R^5$ represents a $C_1$–$C_6$-alkylene or phenylene radical.

Preferred examples of $R^1$ to $R^4$ are methyl, ethyl, propyl, isopropyl, butyl, sec-butyl, tert-butyl, amyl, methylene, ethylidene, phenyl, or benzyl; and preferred examples of $R^5$ are methylene, ethylene, propylene, or phenylene. In a particularly preferred embodiment, Q⁺ represents N-butylpyridinium, N-ethylpyridinium, 3-butyl-1-methylimidazolium, diethylpyrazolium, 3-ethyl-1-methylimidazolium, pyridinium, trimethylphenylammonium, or tetrabutylphosphonium. In a very particularly preferred embodiment, Q⁺ represents 3-butyl-1-methylimidazolium, N-butylpyridinium, or N-methylpyridinium.

In the formula Q⁺ A⁻, A⁻ preferably represents hexafluorophosphate, hexafluoroantimonate, hexafluoroarsenate, fluorosulfonate, tetrafluoroborate, nitrate, alkylsulfonate, or hydrogen sulfate. A⁻ particularly preferably represents tetrafluoroborate, nitrate, methylsulfonate, propylsulfonate, or hydrogen sulfate.

Very particularly preferred compounds Q⁺ A⁻ are 3-butyl-1-methylimidazolium tetrafluoroborate, 3-butyl-1-methylimidazolium methylsulfonate, 3-butyl-1-methylimidazolium propylsulfonate, N-butylpyridinium methylsulfonate, and N-methylpyridinium hydrogen sulfate.

In the process of the invention, it is also possible to use mixtures of various ionic liquids.

In the process of the present invention, an ionic liquid or a mixture of various ionic liquids is preferably used in a 1- to 10-fold molar excess, particularly preferably in a 2- to 6-fold molar excess, very particularly preferably in a 2- to 5-fold molar excess, based on naphthalene.

The process of the invention can usually be carried out at temperatures of from 50 to 110° C., preferably at temperatures of from 60 to 100° C. and particularly preferably at temperatures of from 80 to 100° C.

The process of the invention can be carried out without additional solvent in a mixture of at least one ionic liquid and nitric acid, if desired in the presence of sulfuric acid and/or phosphoric acid. In a further embodiment, the process of the invention can also be carried out after addition of a solvent. Suitable solvents are, for example, all solvents that are stable under the conditions of the nitration, preferably ligroin, chloroform, dichloromethane, or cyclohexane.

The process of the invention is preferably carried out without addition of a solvent.

To carry out the process of the invention, naphthalene, at least one ionic liquid, and the acid used are mixed. To ensure complete reaction, the reaction can be carried out with good mixing of the reaction mixture, for example, by intensive stirring. The reaction time is usually in the range from 30 minutes to 20 hours, preferably in the range from 2 to 18 hours. The work-up can be carried out by introducing the reaction mixture into water and subsequent extracting with organic solvent, preferably a nitrated organic solvent, particularly preferably nitrobenzene. If the work-up of the reaction mixture is carried out by extraction with an organic solvent, the solvent can be removed by means of measures known to those skilled in the art, for example, distillation.

The dinitronaphthalene isomer mixture can be separated into the isomeric dinitronaphthalenes in a known manner, for example, by fractional crystallization. Such isomer separations, for example, using dimethylformamide or dichloroethane as solvent, have been described previously (Houben-Weyl, *Methoden der organischen Chemie*, 1971, Vol. 10, p. 494).

The following examples further illustrate details for the process of this invention. The invention, which is set forth in the foregoing disclosure, is not to be limited either in spirit or scope by these examples. Those skilled in the art will readily understand that known variations of the conditions of the following procedures can be used. Unless otherwise noted, all temperatures are degrees Celsius and all percentages are percentages by weight.

EXAMPLES

Example 1

Nitration of naphthalene using nitric acid in the presence of N-methylpyridinium hydrogen sulfate 64 mg of naphthalene (0.5 mmol) and 0.5 g of N-methylpyridinium hydrogen sulfate (2.6 mmol) were added to 1 g of 98% (w/w) nitric acid (16 mmol). The mixture was subsequently stirred at 100° C. for 4 hours. The work-up was carried out by introduction of the reaction mixture into 20 ml of ice water and subsequent extraction with nitrobenzene.

The isomer composition of the mixture was determined by gas chromatography. The values reported are effective contents (the combustion factors of the two isomers were taken into account).

| | |
|---|---|
| 1,5 Dinitronaphthalene: | 38% |
| 1,8 Dinitronaphthalene: | 53% |
| Other dinitronaphthalenes: | 9.3% |
| Conversion: | 100% |

The further Examples 2 to 9 were carried out as described in Example 1 using the parameters shown in Table 1.

TABLE 1

| Ex. | Acid | Equivs. nitric acid based on nitro groups to be introduced | Ionic liquid* | Equivs. ionic liquid based on naphthalene | Temperature [° C.] | Time [h] | 1,5-Dinitro-naphthalene [%] | 1,8-Dinitro-naphthalene [%] | Other dinitro-naphthalenes [%] | Ratio of 1,5-dinitro-naphthalene to 1,8-dinitro-naphthalene | Conversion [%] |
|---|---|---|---|---|---|---|---|---|---|---|---|
| 1 | $HNO_3$ 98% | 16 | MePyHSO$_3$ | 5.0 | 100 | 4 | 38 | 53 | 9 | 0.72 | 100 |
| 2 | $HNO_3$ 98% | 8 | MeBulmMeSO$_3$ | 4.5 | 80 | 4 | 38 | 50 | 12 | 0.76 | 66 |
| 3 | $HNO_3$ 98% | 8 | MeBulmPrSO$_3$ | 4.0 | 100 | 16 | 38.5 | 52 | 10 | 0.74 | 74 |
| 4 | $HNO_3$ 98% | 8 | MePyHSO$_4$ | 5.0 | 100 | 2 | 36.5 | 51 | 12.5 | 0.72 | 94 |
| 5 | $HNO_3$ 80–98% | 22 | MePyHSO$_4$ | 5.0 | 100 | 2 | 39 | 51.5 | 9.5 | 0.76 | 89 |
| 6 | $HNO_3$ 67% $H_2SO_4$ 98% (2:1) | 12 | MeBulmBF$_4$ | 5.0 | 100 | 18 | 38.5 | 52 | 9.5 | 0.74 | 98 |
| 7 | $HNO_3$ 98% $H_2SO_4$ 98% (2:1) | 12 | MeBulmBF$_4$ | 4.5 | 100 | 18 | 38.5 | 52 | 9.5 | 0.74 | 97 |
| 8 | $HNO_3$ 98% $H_2SO_4$ 98% (2:1) | 12 | MePyHSO$_4$ | 5.0 | 100 | 4 | 37 | 50 | 13 | 0.73 | 75 |
| 9 | $HNO_3$ 98% $H_2SO_4$ 98% (2:1) | 12 | MePyHSO$_4$ | 5.0 | 100 | 16 | 38 | 50 | 12 | 0.76 | 87 |

*MeBulmMeSO$_3$ represents 3-butyl-1-methylimidazolium methylsulfonate, MeBulmPrSO$_3$ represents 3-butyl-1-methylimidazolium propylsulfonate, MePyHSO$_4$ represents N-methylpyridinium hydrogen sulfate, and MeBulmBF$_4$ represents 3-butyl-1-methylimidazolium tetrafluoroborate

What is claimed is:

1. A process for preparing a dinitronaphthalene isomer mixture having an increased proportion of 1,5-dinitronaphthalene comprising nitrating naphthalene with a molar excess of nitric acid in the presence of at least one ionic liquid of the formula $Q^+ A^-$ that is liquid at a temperature below 90° C., wherein
    $Q^+$ represents a quaternary ammonium and/or phosphonium ion and
    $A^-$ represents an anion selected from the group consisting of hexafluorophosphate, hexafluoroantimonate, hexafluoroarsenate, fluorosulfonate, tetrafluoroborate, nitrate, alkylsulfonate, and hydrogen sulfate.

2. A process according to claim 1 wherein the nitric acid is used in a 1- to 22-fold molar excess, based on the nitro groups to be introduced into naphthalene.

3. A process according to claim 1 wherein the nitric acid is 50–100% strength nitric acid.

4. A process according to claim 1 wherein the nitric acid is used in admixture with sulfuric acid and/or phosphoric acid.

5. A process according to claim 4 wherein the sulfuric acid is 90–100% strength sulfuric acid and the phosphoric acid is 50–99% strength phosphoric acid.

6. A process according to claim 4 wherein from 1 to 20 molar parts of nitric acid are used per 1 molar part of sulfuric acid and/or phosphoric acid.

7. A process according to claim 1 wherein $Q^+$ represents a quaternary ammonium and/or phosphonium ion selected from the group consisting of $R^1R^2R^3R^4N^+$, $R^1R^2N^+{=}CR^3R^4$, $R^1R^2R^3R^4P^+$, $R^1R^2P^+{=}CR^3R^4$,

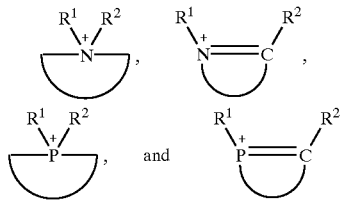

wherein
    $R^1$, $R^2$, $R^3$, and $R^4$ are identical or different and are each hydrogen (with the proviso that $R^1R^2R^3R^4N^+$ cannot be $NH_4^+$), saturated or unsaturated $C_1$–$C_{12}$-alkyl, $C_3$–$C_8$-cycloalkyl, $C_6$–$C_{10}$-aryl, or $C_7$–$C_{11}$-aralkyl and
    the rings contain from 4 to 10 atoms.

8. A process according to claim 1 wherein the ionic liquid is 3-butyl-1-methylimidazolium tetrafluoroborate, 3-butyl-1-methylimidazolium methylsulfonate, N-butylpyridinium methylsulfonate, 3-butyl-1-methylimidazolium propylsulfonate, or N-methylpyridinium hydrogen sulfate.

9. A process according to claim 1 wherein the ionic liquid is used in a 1- to 10-fold molar amount, based on the amount of naphthalene.

* * * * *